United States Patent [19]

Gardlik

[11] Patent Number: 4,883,888
[45] Date of Patent: Nov. 28, 1989

[54] OXA-FENCHYL AMINES USEFUL FOR PREPARING HIGH INTENSITY SWEETENERS

[75] Inventor: John M. Gardlik, Cincinnati, Ohio

[73] Assignee: The Procter & Gamble Company, Cincinnati, Ohio

[21] Appl. No.: 630,464

[22] Filed: Jul. 13, 1984

[51] Int. Cl.$^4$ ............................................ C07D 307/00
[52] U.S. Cl. .................................. 549/463; 549/355; 549/347
[58] Field of Search ........................ 549/463, 355, 397

[56] References Cited

U.S. PATENT DOCUMENTS 4,353,922  10/1982  Pfister .................................. 260/326

FOREIGN PATENT DOCUMENTS 81893  6/1983  European Pat. Off. ............ 549/463

OTHER PUBLICATIONS

Yamada et al., "A New Type of Olefinic Cyclization of Geraniol with Thallium (III) Perchlorate," *J. Chem. Soc. Chem. Comm.*, (1976), pp. 997–98.

Nace *Organic Reactions*, vol. 12, (1966), pp. 57–90.

Meinwald et al., "Highly Strained Bicyclic System: The Synthesis of Optically Active 2 Alpha-and 2 Beta–Amino and Hydroxy Bicyclo [2,1,1] Hexanes," *J. Amer. Chem. Soc.*, vol. 82, (1960), pp. 5445–5450.

Brown et al., "Selective Reductions: The Stereochemistry of Reduction of Cyclic and Bicyclic Ketones by the Alkoxy-Substituted Lithium Aluminum Hydrides," *J. Am. Chem. Soc.*, vol. 87, (1965), pp. 5620–5625.

Tabushi et al., "Sulfur–Carbonyl Interaction in Rigid Beta–Keto Sulfides," *Bull. Chem. Soc. Jap.*, vol. 51, (1978), pp. 1178–1182.

Tabushi et al., "Solvolyses of 2-Endo-and 2-Exo-Chloro-7-Thiabicyclo(2.2.1) Heptanes," *J. Am. Chem. Soc.;* vol. 97, (1975), pp. 2886–2891.

Tabushi et al., "The Extrusion Reaction of Sulfur Dioxide from Strained Sulfolene," *Tet. Lett.*, No. 44, (1976), pp. 3957–3960.

Mariano et al., "Photochemistry of N–Allyliminium Salts: A Novel Photocyclization Reaction Leading to Pyrrolidines," *J. Am. Chem. Soc.*, vol. 99, (1977), pp. 6781–6782.

Kaiser et al., "Natural Occurrence of New Ionone Derivatives and Their Structural Assignments by Synthetic Approaches," *Int'l. Congr. Essent. Oils 7th*, vol. 7, (1979), pp. 395–399.

*Primary Examiner*—Mary C. Lee
*Assistant Examiner*—Bernard I. Dentz
*Attorney, Agent, or Firm*—Eric W. Guttag; David K. Dabbiere; Richard C. Witte

[57] ABSTRACT

Oxa-fenchols and oxa-fenchyl amines are disclosed which are useful in the preparation of high intensity sweeteners. These sweeteners can be used to sweeten a variety of foods, beverages and other oral products. The oxa-fenchols also have a pine-like fragrance which makes them potentially useful as a perfume ingredient.

2 Claims, No Drawings

OXA-FENCHYL AMINES USEFUL FOR PREPARING HIGH INTENSITY SWEETENERS

TECHNICAL FIELD

The present application relates to oxa-fenchols and oxa-fenchyl amines useful in the preparation of high intensity sweeteners.

Sweeteners are used in a variety of orally ingested products. For example, sweeteners are an important component of cakes, cookies, chewing gum, dentifrices and the like. Sweeteners are a particularly important ingredient in beverages. In terms of volume, carbonated beverages use more sweeteners than any other sweetened product category.

The most widely used sweetener for food, and especially beverage products, is sucrose. Sucrose is safe, naturally occurring, and has a high sweetness quality in terms of a pure, quick onset of sweetness with no aftertaste or undertaste. However, the normal usage of sucrose provides significant caloric load which is undesirable for those persons on weight control or reduction programs. Also, those persons who have diabetes must carefully control their intake of sucrose to avoid problems associated with the disease. Sucrose is also cariogenic so that it cannot be used in dentifrices and is undesirable in chewing gums. Additionally, and perhaps little realized, for the amount of sweetness delivered, sucrose can be expensive relative to other sweeteners such as saccharin, especially when used in carbonated beverages.

The drawbacks of sucrose, including its expense, have led those in the beverage industry to seek substitute sweeteners. One particularly important quality sought in such sweeteners is high sweetness intensity. Sweetness intensity can affect not only the safety profile and caloric value of the sweetener, but also its cost in terms of sucrose equivalent sweetness. However, the inability to predict that a given compound is sweet, and particularly that it has high sweetness intensity, makes the search for suitable substitute sweeteners a "hit-or-miss" proposition.

Such unpredictability is especially true for the currently popular L-aspartic acid derived sweeteners represented by the following formula:

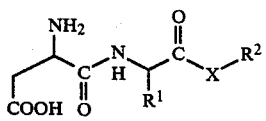

where X is O (ester) or NH (amide). Various theories have been proposed for what imparts sweetness to these particular molecules. However, the current belief is that groups $R^1$ and $R^2$ need to be dissimilar in size for greatest sweetness intensity, i.e. one group large or bulky, the other group small. See Goodman et al., "Peptide Sweeteners: A Model for Peptide and Taste Receptor Interactions," *Proc. 15th Eur. Pep. Symp.*, (1974), pp. 271–78; Sukehiro et al., "Studies on Structure-Taste Relationships of Aspartyl Peptide Sweeteners: Syntheses and Properties of L-Aspartyl-D-Alanine Amides," *Science of Human Life*, Vol. 11, (1977), pp. 9–16. It also appears that when $R^1$ is the large or bulky group, the stereochemical configuration generally needs to be L, L for sweetness. See U.S. Pat. No. 3,972,860 to Moriarty et al., issued Aug. 3, 1976 (L-aspartyl-L-phenylglycine lower alkyl esters are sweet); U.S. Pat. No. 3,492,131 to Schlatter, issued Jan. 27, 1970 (L-aspartyl-L-phenylalanine lower alkyl esters are sweet). Conversely, when $R^1$ is the small group, the stereochemical configuration generally needs to be L, D for sweetness. See U.S. Pat. No. 4,411,925 to Brennan et al., issued Oct. 25, 1983 (L-aspartyl-D-alanine amides are sweet); Ariyoshi et al., "The Structure-Taste Relationships of the Dipeptide Esters Composed of L-Aspartic Acid and Beta-Hydroxy-amino Acids," *Bull. Chem. Soc. Jap.*, Vol. 47, (1974), pp. 326–30 (L-aspartyl-D-serine esters are sweet). Even with these guidelines, the sweetness intensity of these L-aspartic acid derived sweeteners can vary greatly depending upon which combination of $R^1$ and $R^2$ groups are selected. Compare U.S. Pat. No. 4,411,925, supra (X is NH, $R^1$ is methyl group, $R^2$ is 2,6-dimethyl cyclohexyl group, sweetness intensity is 600 times that of sucrose), with U.S. Pat. No. 3,907,766 to Fujino et al., issued Sept. 23, 1975 (X is 0, $R^1$ is methyl ester group, $R^2$ is fenchyl group, sweetness intensity is 22,200–33,200 times that of sucrose).

For beverage use, the substitute sweetener must be sufficiently soluble and hydrolytically stable. Most carbonated beverages have a pH of from about 2.5 to about 4.8. Useful sweeteners in such beverages much therefore be relatively resistant to acid catalyzed breakdown. Otherwise, the beverage can quickly lose its sweetness or possibly have undesirable off-flavors imparted to it. As in the case of sweetness intensity, it can be difficult to predict whether a given sweetener will be hydrolytically stable, especially in an acidic environment.

Other factors are also important in providing a useful substitute sweetener. To obtain approval for food or beverage use, the substitute sweetener must be safe in terms of acute toxicity as well as long-term effects from continued use. The substitute sweetener should also desirably approach sucrose in terms of sweetness quality, as well as have a relatively quick onset and short duration of sweetness. Finally, to be classified as a non-caloric sweetener, the substitute sweetener (or metabolic products thereof) should provide minimal or no caloric value at normal usage levels.

The most widely used substitute sweetener at present is saccharin, in particular its sodium salt. Saccharin has a relatively high sweetness intensity (about 300 times that of sucrose) and is relatively inexpensive in providing sucrose equivalent sweetness in carbonated beverages. However, saccharin also provides an undesirable lingering bitter aftertaste.

Besides saccharin, a number of the L-aspartic acid derived amides have been proposed as suitable substitute sweeteners. The most prominent examples are the alpha-L-aspartyl-L-phenyl-alanine lower alkyl esters, in particular the methyl ester known as aspartame. Aspartame has been approved for use in dry foods and beverages, and has recently been approved for use in aqueous beverage systems such as carbonated beverages. The sweetness intensity of aspartame is about 150–200 times that of sucrose with a sweetness quality approaching that of sucrose. The caloric value of aspartame is also relatively minimal at normal usage levels. However, aspartame is hydrolytically unstable in most carbonated beverages. Perhaps more important to the beverage industry, aspartame is extremely expensive in terms of sucrose equivalent sweetness delivered.

The search therefore continues for substitute sweeteners which are: (1) inexpensive in terms of sucrose equivalent sweetness; (2) are hydrolytically stable in carbonated beverage systems; (3) are safe; (4) have satisfactory taste quality; and (5) provide minimal caloric value.

BACKGROUND ART

Yamada et al, "A New Type of Olefinic Cyclization of Geraniol with Thallium (III) Perchlorate," *J. Chem. Soc. Chem. Comm.*, (1976), pp. 997-98, discloses the conversion of geraniol to the respective bicyclic alcohol by using thallium (III) perchlorate.

Nace, *Organic Reactions*, Vol. 12, (1966), pp. 57-90, discloses the conversion of primary alcohols, including bicyclic alcohols, to the respective xanthate esters by using sodium hydride, carbon disulfide and methyl iodide. Pyrolysis of the xanthate ester gives the respective methylene substituted compound. See pp. 75-88, 80.

Meinwald et al, "Highly Strained Bicyclic System: The Synthesis of Optically Active 2α- and 2β-Amino and Hydroxy Bicyclo[2,1,1]Hexanes" *J. Amer. Chem. Soc.*, Vol. 82, (1960), pp. 5445-50, discloses the conversion of methylene substituted bicyclics to the respective ketones by using ozone, KI and acetic acid. See pp. 5446 and 5448.

Brown et al, "Selective Reductions: The Stereochemistry of Reduction of Cyclic and Bicyclic Ketones by the Alkoxy-Substituted Lithium Aluminum Hydrides," *J. Amer. Chem. Soc.*, Vol. 87 (1965), pp. 5620-25, discloses the reduction of bicyclic ketones to the respective alcohols. See pp. 5622.

DISCLOSURE OF THE INVENTION

The present invention relates to oxa-fenchols, oxa-fenchyl amines, and like bicyclic alcohols and amines. These bicyclic alcohols and amines are selected from those having formulas (a), (b), and (c).

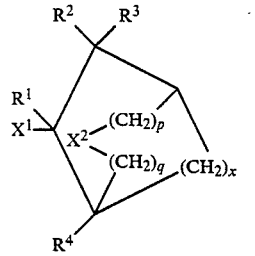

(a)

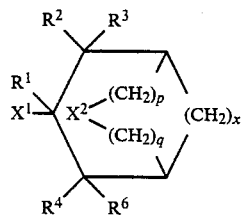

(b)

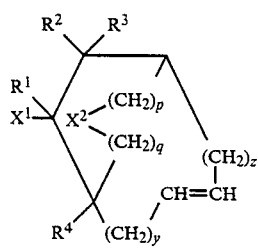

(c)

wherein $R^1$, $R^2$, $R^3$, $R^4$ and $R^5$ are H, or $C_1$-$C_4$ alkyl, hydroxyalkyl or alkoxy; provided that at least one of $R^2$, $R^3$, $R^4$ and $R^5$ are $C_1$-$C_4$ alkyl, hydroxyalkyl or alkoxy; $X^1$ is OH or $NH_2$; $X^2$ is O; p and q are 0, 1, 2, or 3 and the sum of p+q is not greater than 3; x is 1, 2, or 3; y and z are 0, 1 or 2 and the sum of y+z is not greater than 2.

The oxa-fenchols and oxa-fenchyl amines of the present invention are useful in the preparation of alpha-L-aspartyl-D-phenylglycine ester and amide sweeteners disclosed in U.S. application Ser. No. 630,457 to John M. Janusz and John M. Gardlik filed July 13, 1984 now abandoned. These alpha-L-aspartyl-D-phenylglycine esters and amides are more hydrolytically stable in carbonated beverages than aspartame. Also, certain of these esters and amides have sufficiently high sweetness intensity so as to be relatively inexpensive in terms of sucrose equivalent sweetness. Based on available data for the expected metabolites, it is believed that these esters and amides are safe for use in food and beverage systems, and will provide minimal caloric value at normal usage levels. The taste quality of these sweeteners is also satisfactory. The oxa-fenchols also have a pine-like fragrance which makes them potentially useful as a perfume ingredient. perfume ingredient.

A. OXA-FENCHOLS AND OXA-FENCHYL AMINES

The bicyclic alcohols and amines of the present invention are selected from those having one of three formulas. The first group have formula (a):

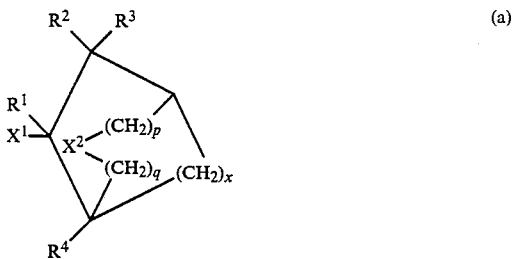

(a)

wherein $R^1$, $R^2$, $R^3$ and $R^4$ are H or $C_1$-$C_4$ alkyl, hydroxyalkyl or alkoxy; provided that at least one of $R^2$, $R^3$, $R^4$ and $R^5$ are $C_1$-$C_4$ alkyl, hydroxyalkyl or alkoxy; $X^1$ is OH or $NH_2$; $X^2$ is O; p and q are each 0, 1, 2, or 3; the sum of p+q being not greater than 3; and x is 1, 2 or 3. Preferably $R^2$, $R^3$ and $R^4$ are methyl or H; $R^1$ is preferably H; the sum of p+q is preferably 0; x is preferably 2. Especially preferred radicals of formula (a) are alpha-7-oxa-fenchol; beta-7-oxa-fenchol alpha-7-oxa-fenchyl amine; and beta-7-oxa-fenchyl amine.

The second group have the formula (b):

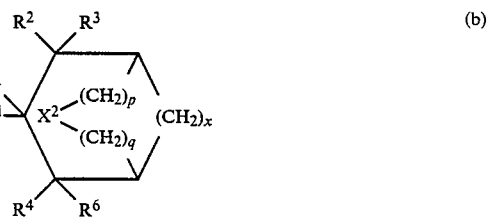

(b)

wherein $R^1$, $R^2$, $R^3$, $R^4$, $X^1$, $X^2$, p, q and x are defined as before; and $R^5$ is H or $C_1$-$C_4$ alkyl, hydroxyalkyl, or alkoxy. Preferably $R^2$, $R^3$, $R^4$ and $R^5$ are methyl or H;

R[1] is preferably H; the sum of p+q is preferably 0; x is preferably 2.

The third group have the formula (c):

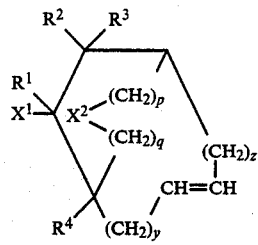

wherein R[1], R[2], R[3], R[4], X[1], X[2], p and q are defined as before; and y and z are 0, 1 or 2 and the sum of y+z is no greater than 2. Preferably, R[2], R[3] and R[4] are H or methyl; R[1] is preferably H; the sum of p+q is preferably 0; the sum of y+z is preferably 0 or 1.

B. PROCESS FOR MAKING OXA-FENCHOLS AND OXA-FENCHYL AMINES

The oxa-fenchols and oxa-fenchyl amines of the present invention can be made according to the following 4-step reaction scheme:

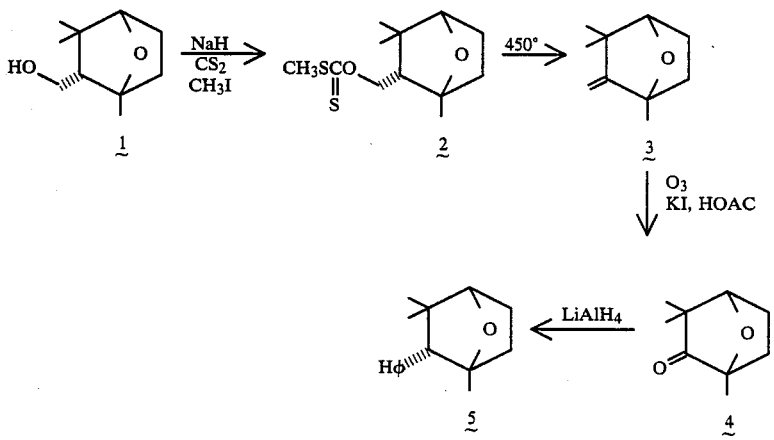

In the first step, alcohol 1 is converted to the xanthate ester 2 by using NaH, carbon disulfide and methyl iodide. In the second step, xanthate ester 2 is thermally decomposed to the methylene substituted bicyclic compound 3. In the third step, bicyclic compound 3 is converted to ketone 4 by using ozone, KI and acetic acid. In the fourth step, ketone 4 is reduced to alcohol 5. Amines can be obtained from the respective ketone 4 by the oxime procedure described in U.S. Pat. No. 4,411,925 to Brennan et al, issued Oct. 25, 1983 (herein incorporated by reference), especially column 12, line 55 to column 20, line 9, and Example 47.

The synthesis of (±)-alpha-7-oxa-fenchol is as follows:

EXAMPLE 1

Step 1:
(±)-endo-1,3,3-Trimethyl-7-oxabicyclo[2.2.1]heptane-2-methanol

Geraniol was converted to (±)-endo-1,3,3-trimethyl-7-oxabicyclo-[2.2.1]heptane-2-methanol using thallium (III) perchlorate according to the procedure described in Yamada et al., *J. Chem. Soc. Chem. Comm.*, (1976), page 997.

Step 2: S-methyl xanthate ester of (±)-endo-1,3,3-trimethyl-7-oxabicyclo[2.2.1]heptane-2-methanol (±)-endo-1,3,3,-Trimethyl-7-oxabicyclo[2.2.1]heptane-2-methanol from step 1 (2.1 g, 0.013 moles) was slowly added to a suspension of NaH (0.90 g., 0.038 moles) in 100 ml. of tetrahydrofuran (THF) at 0° C. under argon. After stirring at 0° C. for 5 minutes, the reaction mixture was refluxed for 2 hours. Carbon disulfide (2.9 g., 0.038 moles) was added dropwise and the reaction mixture was refluxed for 1 hour. Methyl iodide (5.35 g., 0.037.7 moles) was then added dropwise and the reaction mixture was refluxed for an additional 2 hours. At this point, the reaction mixture was cooled to room temperature, $H_2O$ was slowly added until two phases formed, the layers were separated, and the aqueous layer was extracted with ether. The organic layers were combined, washed successively with $H_2O$ and brine, and then dried over $MgSO_4$. Evaporation of the solvent and vacuum distillation of the residue afforded the xanthate ester as an amber oil. Yield: 2.78 g. The distilled product was characterized by NMR.

Step 3:
(±)-1,3,3-Trimethyl-2-methylidine-7-oxabicyclo[2.2.1]heptane

The xanthate ester from step 2 (2.78 g., 0.011 moles) was pyrolyzed in the vapor phase at 450° C., 0.1 mm. pressure using a glass tube packed with glass beads heated by a cylindrical furnace. The product was collected using two traps connected in series, both cooled to −78° C. Yield: 1.27 g. The crude product was characterized by NMR.

Step 4:
(±)-1,3,3-Trimethyl-7-oxabicyclo[2.2.1]heptane-2-one

A stream of 3-5% ozone in oxygen was passed through a solution of (±)-1,3,3-trimethyl-2-methylidine-7-oxabicyclo[2.2.1]heptane from step 3 (1.20 g, 0.007 moles) in 35 ml. of methanol at −78° C. until the solution became light blue (ozone saturation). The excess ozone was removed by purging the cold reaction mixture with oxygen for 15 minutes. The cold reaction mixture was then poured into a stirred solution of 15 ml. of methanol, 4 ml. of glacial acetic acid, and 8 g. of sodium iodide and stirred for 30 minutes. Sodium thiosulfate solution (0.1N) was added to decompose the liberated iodine. Saturated sodium bicarbonate solution was then added until the mixture was slightly basic (pH 7.5). The aqueous mixture was extracted with ether, the extract washed with brine, and then dried over Na$_2$SO$_4$. Evaporation of the solvent afforded the product which was characterized by NMR. Yield: 1.12 g.

Step 5:
($\pm$)-endo-2-Hydroxy-1,3,3-trimethyl-7-oxabicyclo[2.2.1]-heptane (($\pm$)-alpha-7-oxa-fenchol)

A 1M solution of LiAlH$_4$ in ether (15 ml., 0.015 moles) was added dropwise to a solution of ($\pm$)-1,3,3-trimethyl-7-oxabicyclo[2.2.1]heptane-2-one from step 4 (1.10 g, 0.006 moles) in 50 ml. of THF at 0° C. The reaction mixture was stirred for 30 minutes, and then quenched by the careful addition of saturated Na$_2$SO$_4$ solution. The resulting white precipitate was removed by vacuum filtration and washed with ether. The filtrate was evaporated, affording the product as a colorless oil which was characterized by NMR. Yield: 0.82 g.

C. ALPHA-L-ASPARTYL-D-PHENYLGLYCINE ESTERS AND AMIDES

The oxa-fenchols and oxa-fenchyl amines are used to prepare esters and amides sweeteners of the following formula:

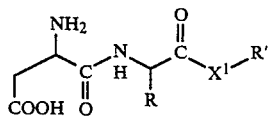

wherein the ester or amide is the L, D stereochemical isomer; wherein X$^1$ is O or NH; wherein R is a phenyl group; and wherein R' is derived from the respective bicyclic alcohols and amines as previously defined in the present application.

It has been determined that the L,D stereochemical isomer imparts the sweetness character to these esters and amides. However, minor amounts of the D,L, L,L and D,D stereochemical isomers can be tolerated without adversely affecting the taste quality of L,D stereochemical isomer. Such diastereomeric mixtures typically comprise at least about 50% of the L,D stereochemical isomer, preferably at least about 70% of the L,D isomer, and most preferably at least about 95% of the L,D isomer.

The esters or amides can be in the form of non-toxic salts. As used herein, "non-toxic salts" means salts of the present esters and amides which are physiologically acceptable for ingestion. Such salts include both cationic and acid addition salts of these esters and amides. By "cationic salts" is meant those salts formed by neutralization of the free carboxylic acid group of the instant esters and amides by bases of physiologically acceptable metals, ammonia and amines. Examples of such metals are sodium, potassium, calcium and magnesium. Examples of such amines are n-methyl-glucamine and ethanolamine. By "acid addition salts" is meant those salts formed between the free amino group of the instant esters and amides and a physiologically acceptable acid. Examples of such acids are acetic, benzoic, hydrobromic, hydrochloric, citric, fumaric, gluconic, lactic, maleic, malic, sulfuric, sulfonic, nitric, phosphoric, saccharic, succinic and tartaric acids.

The compounds can be in the form of either esters or amides (X$^1$ is O or NH). The amides are desirable from the standpoint of having greater hydrolytic stability than the esters. However, the esters have acceptable hydrolytic stability and in particular have a hydrolytic stability greater than that of aspartame. Also, in terms of sweetness intensity, the esters tend to have a greater sweetness intensity.

The phenyl group R of the esters or amides has the formula:

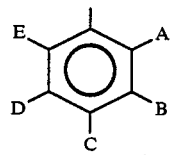

wherein A, B, C, D and E are H, OH, F, Cl, Br or C$_1$-C$_4$ alkyl, hydroxyalkyl or alkoxy. Preferred groups R are those where A, B, C, D and E are all H or where one of A, B, C, D and E is OH or F. Particularly preferred groups R are phenyl (A, B, C; D and E are H), p-hydroxyphenyl (C is OH; A, B, D and E are H) and o-fluorophenyl (A is F; B, C, D and E are H).

D. SWEETNESS INTENSITY OF ALPHA-L-ASPARTYL-D-PHENYLGLYCINE ESTERS AND AMIDES

The sweetness intensity of the esters and amides relative to sucrose can be determined according to the following procedure:

Male subjects are chosen at random from a group of about 20 persons who have previously been selected on the basis of proven tasting acuity, i.e., persons who could easily recognize the four basic tastes (sweet, sour, bitter and salty) and who are adept at quantifying their own physiological response numerically. The subjects are asked to taste and expectorate about 10 ml of a test sample (temperature of about 22° C.) having dissolved therein the ester or amide. The subjects are then asked to compare the sweetness of the test sample with five standard samples which contain increasing amounts of sucrose. The standard samples are letter coded A, B, C, D and E and are designated on a ballot by a closed linear scale. Sweetness intensity of the test sample is recorded by the subject making a mark on the linear scale at a point he considers equal in sweetness among the standard samples; interpolation between standards is encouraged. After completion of the panel, a five point numeric scale is superimposed on the linear scales to obtain numerical data; data are averaged and recorded to the nearest 0.25 unit. Equivalent sucrose sweetness is determined by referring to graphs of (w/v) sucrose concentration in the standard samples versus a linear numeric scale.

Sweetness intensity is calculated by dividing the concentration (w/v) of perceived sweetness by the concentration (w/v) of the ester or amide required to produce that sweetness. The five point scale with standard samples ranging from 1.37% (0.040M) to 11.97% (0.35M) sucrose is used for sweetness intensity testing. The test sample was prepared at a concentration which would be equal to about 8–10% sucrose.

The sweetness intensity of the esters and amides is presented in the following table:

| R Group | Type  | R Group         | Sweetness (x Sucrose) |
|---------|-------|-----------------|----------------------|
| Phenyl  | Ester | alpha-7-oxa-fenchyl | 1000* |

*based on informal panel testing

E. SYNTHESIS OF ALPHA-L-ASPARTYL-D-PHENYLGLYCINE ESTERS AND AMIDES

The alpha-L-aspartyl-D-phenylglycine esters can be synthesized according to the following 4-step reaction scheme:

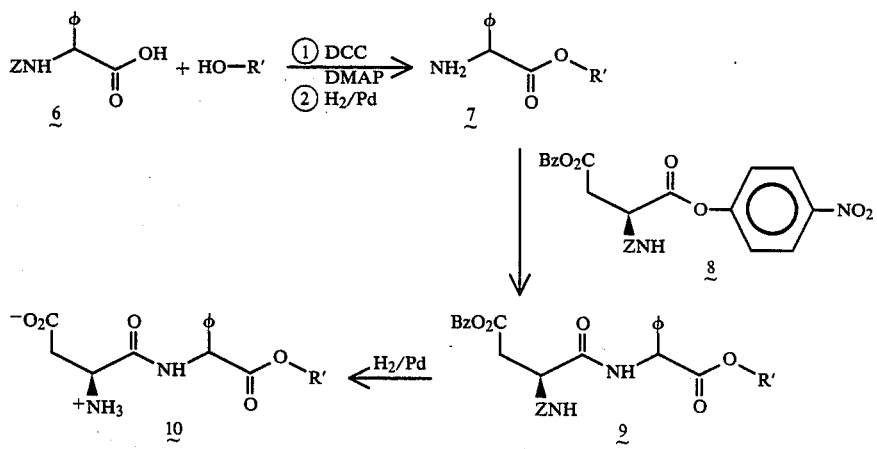

In the first step, carobenzoxy (Z) protected D-phenylglycine 6 is coupled with alcohol R'OH using dicyclohexylcarbodiimide (DCC)/dimethylaminopyridine (DMAP). In the second step, the ester formed in step 1 is hydrogenated over palladium to remove the protecting group to form the phenylglycine ester 7. In the third step, ester 7 is coupled to the protected activated L-aspartic ester 8 to form the protected L-aspartyl-D-phenylglycine ester 9. In the fourth step, the protecting groups are removed by hydrogenation of ester 4 over palladium to yield sweetener 10.

Syntheses of specific alpha-L-aspartyl-D-phenylglycine esters are as follows:

EXAMPLE 2:

ALPHA-7-OXA-FENCHYL ESTER

Step 1: N-Carbobenzyloxy-D-phenylglycine-(±)-alpha-7-oxa-fenchyl ester a. N-Carbobenzyloxy-D-phenylglycine To D-phenylglycine (50 g., 0.33 moles, Aldrich) is added 82 ml. of 4N NaOH. The mixture is cooled to 0° C. and carbobenzoxy chloride (51 ml., 0.36 moles) is added dropwise. Additional NaOH is added as needed to keep the reaction mixture basic. After stirring for 10 minutes, 200 ml. of $H_2O$ is added. After 10 more minutes, the solution is filtered. The clear filtrate is extracted twice with ether and is then adjusted to pH 3 with 5N HCl. The resulting precipitate is filtered, washed twice with $H_2O$ and then dried. The crude product is dissolved in ethyl acetate and then filtered. The filtrate is evaporated and the resulting solid crystallized from ethyl acetate/hexane.

b. (±)-alpha-7-oxa-Fenchol (±)-alpha-7-oxa-Fenchol is prepared according to the procedure of Example 1.

c. N-Carbobenzyloxy-D-phenylglycine-(±)-alpha-7-oxa-fenchyl ester

The N-carbobenzyloxy-D-phenylglycine (20 g., 0.07 moles) from step 1a is dissolved in about 150 ml. of dry methylene chloride. The (±)-alpha-7-oxa-fenchol (10.9 g., 0.07 moles) from step 1b and N,N'-dicyclohexylcarbodiimide (17.3 g., 0.083 moles) are then added after cooling the solution to 0° C. The mixture thickens; additional methylene chloride (about 150 ml.) is added. When the mixture becomes more uniform, it is then chilled to −65° C. 4-Dimethylaminopyridine is then added and the mixture stirred at −60° to −65° C. for 1 hour. The cooling bath is then changed to carbon tetrachloride/dry ice to maintain the mixture at −23° C. for 3 hours. The precipitated N,N'-dicyclohexylurea is filtered off. The filtrate is successively washed with chilled $H_2O$, 0.1N HCl, 2% $NaHCO_3$, $H_2O$ and brine. The filtrate is dried over $MgSO_4$, filtered and then evaporated.

Step 2: D-phenylglycine-(±)-alpha-7-oxa-fenchyl ester

To a Parr flask is added 5% palladium on charcoal (200 mg.). The crude ester (28.8 g.) from step 1c in about 200 ml. of methanol is then added. The contents of the flask are hydrogenated for 5 hours. Additional 5% palladium on charcoal (200 mg.) plus 10% palladium on charcoal (100 mg.) is added to the flask and hydrogenation is continued overnight. The contents of the flask are then filtered and evaporated to yield the crude product. This crude product is dissolved in 0.1N HCl and is extracted twice with ether to remove nonbasic impurities. The aqueous layer is adjusted to pH 9–10 with NaOH and is then extracted 3 times with ether. The combined extracts are successively washed with $H_2O$ and brine, and then dried over $MgSO_4$. The dried extracts are filtered and then evaporated to give the desired ester.

Step 3:

beta-Benzyl-N-carbobenzyloxy-L-aspartyl-D-phenylg-lycine-(±)-alpha-7-oxa-fenchyl ester a.
Beta-benzyl-N-carbobenzoxy-L-aspartyl-p-nitrophenyl ester

To a 1000 ml. 3-neck flask is added beta-benzyl-N-carbobenzyloxy-L-aspartic acid (50 g., 0.14 moles, Bachem Inc.), p-nitrophenol (23.5 g., 0.17 moles) and about 350 ml. of ethyl acetate. This mixture is stirred and then 4-dimethylaminopyridine (1.0 g.) and N,N'-dicyclohexylcarbodiimide (28.5 g., 0.14 moles) is added. The solution becomes warm; after 4 hours, the reaction is complete as measured by thin layer chromatography. The solution is then filtered to remove precipitated N,N'-di-cyclohexylurea and then extracted 9 times with saturated $Na_2CO_3$ solution, then 2 times with saturated NaCl solution. The extracted solution is dried over $Na_2SO_4$ and then concentrated to yield the crude ester. This concentrated solution is dissolved in hot ethanol and then seeded. The concentrated solution is allowed to fully crystallize at room temperature and is then cooled with ice. The crystals are filtered and then washed with cold ethanol.

b.
beta-Benzyl-N-carbobenzyloxy-L-aspartyl-D-phenylg-lycine-(±)-alpha-7-oxa-fenchyl ester The p-nitrophenyl ester from step 3a (19.6 g., 0.041 moles) is dissolved in 100 ml. of dry tetrahydrofuran (THF) and is chilled to 0° C. The 7-oxa-fenchyl ester from step 2 (11.8 g., 0.041 moles) is added and the reaction mixture is then stirred at 0° C. for 1 hour. The reaction mixture is stirred overnight at room temperature and then the THF is evaporated. The residue is partitioned between ethyl acetate and $H_2O$. The organic layer is successively washed with cold 10% $Na_2CO_3$, $H_2O$, and brine, and then dried over $MgSO_4$. The dried solution is filtered and then evaporated to give the crude product. This crude product is purified by silica gel chromatography first with 2% acetone/chloroform solvent and then with 25% ethyl acetate/hexane solvent.

Step 4:
alpha-L-Aspartyl-D-phenylglycine-(±)-alpha-7-oxa-fenchyl ester

The purified ester from step 3b (7 g., 0.011 moles) is dissolved in 150 ml. of methanol and is then hydrogenated over 5% palladium on charcoal (300 mg.) for 22 hours. A second portion of the purified ester from step 3b (8 g., 0.013 moles) is hydrogenated over 10% palladium on charcoal (300 mg.) for 5 hours. The catalyst is filtered off and the solvent evaporated for a combined yield of the desired sweetener.

In certain instances, use of carbobenzyloxy protected D-phenylglycine can cause partial racemization at the asymmetric carbon of the phenylglycine moiety during formation of ester 2. Racemization can be minimized by using o-nitrophenylsulfenyl (o-Nps) protected D-phenylglycine to form ester 2 according to the following reactions:

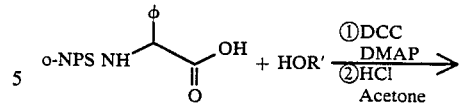

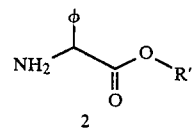

Ester 2 can be converted to the desired ester 5 by the previously described procedure.

Synthesis of specific esters 5 using o-nitrophenylsulfenyl protected D-phenylglycine are as follows:

EXAMPLE 3:

(±)-ALPHA-7-OXA-FENCHYL ESTER

Step 1:
o-Nitrophenylsulfenyl-D-phenylglycine-(±)-alpha-7-oxa-fenchyl ester a: o-Nitrophenylsulfenyl-D-phenylglycine

D-phenylglycine (51 g., 0.34 moles, Aldrich) was dissolved in 180 ml. of 2N NaOH and 200 ml. of dioxane. Then o-nitrophenylsulfenyl chloride (64 g., 0.34 moles) was added in small portions over 1 hour with simultaneous addition of 180 ml. of 2N NaOH. The reaction mixture was stirred for 2 hours and then diluted with 500 ml. of $H_2O$. The mixture was filtered and the solids washed with $H_2O$. The filtrate was acidified with $H_2SO_4$ and then exracted three times with ether. The combined extracts were successively washed with $H_2O$ and brine, dried over $Na_2SO_4$ and then evaporated. The crude product was then recrystallized from ethyl acetate/hexane. Yield: 64.5 g. The purified product was characterized by NMR. $[\alpha]_D = -179.5°$ (C 0.4, methanol).

b: (±)-alpha-7-oxa-Fenchol (±)-alpha-7-oxa-Fenchol was prepared according to the procedure of Example 1.

c.
o-Nitrophenylsulfenyl-D-phenylglycine-(±)-alpha-7-oxa-fenchyl ester

The purified o-Nps-D-phenylglycine from step 1a (1.44 g., 0.005 moles) and (±)-alpha-7-oxa-fenchol from step 1b (0.74 g., 0.005 moles) were dissolved in 50 ml. of $CH_2Cl_2$ and cooled to $-65°$ C. N,N'-dicyclohexylcarbodiimide (1.00 g., 0.005 moles) was added and the mixture then stirred for 20 minutes. A catalytic amount of 4-dimethylaminopyridine (33 mg.) was added and then this reaction mixture was stirred at $-65°$ C. for 1 hour. The reaction mixture was then gradually warmed to $-23°$ C. ($CCl_4$/ice bath) and stirred for 3 hours. The mixture was then filtered and the filtrate washed successively with $H_2O$, 2% $Na_2CO_3$, $H_2O$, and brine. The washed filtrate was dried over $MgSO_4$, filtered and then concentrated to give the crude product. The crude product was purified by flash chromatography on silica gel using 25% ethyl acetate/hexane as the eluting solvent. The purified product was characterized by NMR. Yield: 1.18 g.

Step 2: D-Phenylglycine-(±)-alpha-7-oxa-fenchyl ester

The crude o-Nps-D-phenylglycine-(±)-alpha-fenchyl ester from step 1b (1.10 g., 0.0025 moles) was dissolved in 50 ml. of acetone and 5N HCl (0.5 ml.) was added. The reaction mixture was stirred for 15 minutes and then the acetone was evaporated. The residue was dissolved in 0.1N HCl, was extracted with ether to remove non-basic impurities and was then adjusted to pH 10 with NaOH. The alkaline solution was extracted with ethyl acetate 3 times. The combined extracts were successively washed with $H_2O$ and brine, dried over $MgSO_4$, and then evaporated to give the desired ester. Yield: 0.55 g.

Step 3:
beta-Benzyl-N-carbobenzyloxy-L-aspartyl-D-phenylglycine-(±)-alpha-7-oxa-fenchyl ester By a procedure similar to that of Example 2, Step 3, the ester from step 2 was converted to the diprotected L-aspartyl-D-phenylglycine-(±)-alpha-fenchyl ester. Yield: 0.91 g.

Step 4:
alpha-L-Aspartyl-D-phenylglycine-alpha-7-oxa-fenchyl ester

By a procedure similar to that of Example 2, Step 4, the diprotected ester from step 3 was converted to a mixture of diastereomers from which the desired sweetener (either (+) or (−) oxa-fenchyl ester) was isolated by semi-preparative high performance liquid chromatography using a Whatman Magnum 9 ODS-3 column and 0.01M ammonium acetate in methanol/water (50/50), pH adjusted to 5.4 with acetic acid, as the eluting solvent. The sweetener identity was characterized by NMR. Sweetness intensity: approximately 1000X based on informal panel testing.

The alpha-L-aspartyl-D-phenylglycine amides can also be synthesized according to the previously described schemes for the esters by using a primary amine $R'NH_2$ instead of the alcohol. See U.S. application Ser. No. 630,504 to John M. Janusz filed July 13, 1984 now abandoned, Example 10 for the synthesis of an amide according to this reaction scheme.

The amides can also be synthesized according to the following alternative 4-step reaction scheme:

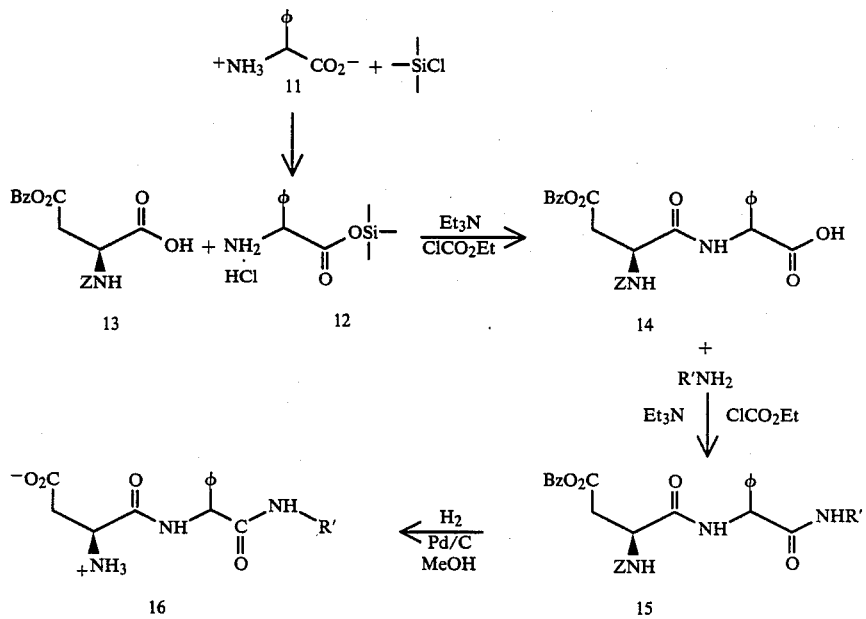

In the first step, D-phenylglycine 11 is reacted with trimethylsilylchloride to form the silyl ester 12. In the second step, silyl ester 12 is coupled to diprotected L-aspartic acid ester 13 using triethylamine and ethyl chloroformate to form diprotected amide 14. In the third step, amine $R'NH_2$ is coupled to diprotected amide 14 using triethylamine and ethyl chloroformate to form diprotected amide 15. In the fourth step, the protecting groups are removed by hydrogenation of amide 15 over palladium to yield sweetener 16. See U.S. application Ser. No. 630,504 to John M. Janusz filed July 13, 1984, Example 12, herein incorporated by reference, for the synthesis of an amide according to this alternative reaction scheme.

The alpha-L-aspartyl-D-p-hydroxyphenylglycine esters can be synthesized according to Example 13 of U.S. application Ser. No. 630,504 to John M. Janusz, filed July 13, 1984, herein incorporated by reference.

F. USES OF ALPHA-L-ASPARTYL-D-PHENYLGLYCINE ESTERS AND AMIDES

The esters or amides can be used to sweeten a variety of edible materials. Also, mixtures of these esters or amides with other sweeteners can be used, in particular, mixtures of these esters or amides with saccharin or its non-toxic salts. As used herein, "non-toxic salts of saccharin" means those salts of saccharin with physiologically acceptable cations such as sodium, potassium, calcium or ammonium. The mixtures of the present esters or amides with saccharin can be in a ratio (sweetness equivalent basis) of from about 2:1 to about 1:9, and preferably from about 1:1 to about 1:4. Mixtures of the present esters and amides with sweeteners other than saccharin can also be used. Examples of such sweeteners include Acesulfam; the alpha-L-aspartyl-L-phenylalanine lower alkyl esters disclosed in U.S. Pat. No. 3,492,131 to Schlatter, issued Jan. 27, 1970 (herein incorporated by reference), in particular the methyl ester known as aspartame; the alpha-L-aspartyl-L-1-hydroxymethylalkyl amides disclosed in U.S. Pat. No. 4,338,346 to Brand, issued July 6, 1982 (herein incorporated by reference); the alpha-L-aspartyl-L-1-hydroxyethylalkyl amides disclosed in U.S. Pat. No. 4,423,029 to Rizzi, issued Dec. 27, 1983 (herein incorporated by reference); the alpha-L-aspartyl-D-alanine amides disclosed in U.S. Pat. No. 4,411,925 to Brennan et al., issued Oct. 25, 1983 (herein incorporated by reference); and the alpha-L-aspartyl-D-serine amides disclosed in U.S. Pat. No. 4,399,263 to Brennan et al., issued Aug. 16, 1983 (herein incorporated by reference). Low calorie mixtures can also be formulated which contain the present esters or amides with sucrose.

The esters and amides, including mixtures thereof with other sweeteners, are useful for sweetening a variety of food products, such as fruits, vegetables, juices, cereals, meat products such as ham or bacon, sweetened milk products, egg products, salad dressings, ice creams and sherbets, gelatins, icings, syrups, cake mixes and frostings. In particular, these sweeteners are useful for sweetening a variety of beverages such as lemonade, coffee, tea, and particularly carbonated beverages. These sweeteners can also be used to sweeten dentifrices, mouthwashes, and chewing gums, as well as drugs such as liquid cough and cold remedies. As an alternative to direct addition of the esters and amides of the present invention to the foregoing edible materials, sweetener concentrates can be prepared using these esters and amides in, for example, granular or liquid form. These concentrates can then be conventionally metered into foods, beverages and the like as desired by the user.

The esters and amides are stable substances that can be used in a variety of physical forms such as powders, granules, tablets, syrups, pastes, solutions and the like. Liquid or solid ingestible carriers such as water, glycerol, starch, sorbitol, salts, citric acid, cellulose and other suitable non-toxic substances can also be used. These sweetening agents can be readily used in pharmaceutical compositions to impart a sweet taste.

The ester and amide sweeteners are used in amounts sufficient to provide a sweet taste of the desired intensity for orally ingested products. The amount of the sweetener added will generally depend upon commercial needs as well as individual sweetness sensitivities.

SPECIFIC EMBODIMENTS OF ORAL PRODUCTS CONTAINING ALPHA-L-ASPARTYL-D-PHENYLGLYCINE ESTERS

A. Beverage

Mixtures of the alpha-7-oxa-fenchyl ester sweetener of Example 3 with other sweeteners are used in cola beverages that are formulated as follows:

| Ingredients | Embodiment 1 (%) | Embodiment 2 (%) |
|---|---|---|
| $H_3PO_4$ | 0.06 | 0.06 |
| Caramel color | 0.25 | 0.25 |
| Flavor | 0.0032 | 0.0032 |
| Saccharin | 0.020 | 0.011 |
| Aspartame | 0.005 | 0.015 |
| Fenchyl ester | 0.0005 | 0.0036 |
| $CO_2$ | 3.5 (volumes) | 3.5 (volumes) |

B. Toothpaste

The following toothpaste formulation is within the scope of the present invention:

| Ingredient | Wt. % |
|---|---|
| Calcium pyrophosphate | 40.00 |
| Sorbitol (70% aqueous solution) | 20.40 |
| Glycerine | 10.20 |
| Sodium coconut monoglyceride sulfonate | 0.80 |
| Sodium carboxymethyl cellulose | 1.20 |
| Sodium coconut alkyl sulfate (20% active) | 2.30 |
| Sodium fluoride | 0.22 |
| Sweetener (Example 3) | 0.016 |
| Flavor | 0.90 |
| Red urea formaldehyde agglomerates | 0.65 |
| Water and minor ingredients | Balance |

C. Mouthwash

A mouthwash according to the present invention is prepared by co-dissolving the following ingredients:

| Ingredient | Percent by Weight |
|---|---|
| Glycerine | 10.00 |
| Ethyl alcohol | 17.00 |
| Cetyl pyridinium chloride | 0.05 |
| Sorbitan monooleate polyoxyethylene | 0.13 |
| Flavor (Oil of Wintergreen) | 0.09 |
| Sweetening agent* | 0.02 |
| Water and minor ingredients | Balance |

*Sweetener of Example 3, Hydrochloride salt

D. Dentifrice

A gel dentifrice having the following formulation is prepared by conventional means:

| Ingredients | Percent by Weight |
|---|---|
| Silica xerogel | 12.00 |
| Silica aerogel | 5.00 |
| Hydroxyethyl cellulose | 1.50 |
| Glycerine | 34.76 |
| Stannous fluoride | 0.41 |
| Flavor (Wintergreen) | 0.95 |
| Color (FD&C Blue #1) | 0.03 |
| 21% sodium lauryl sulfate-79% glycerine mixture | 6.00 |
| Sweetener* | 0.012 |
| Water and minor ingredients | Balance |

*Example 3, Calcium salt.

The above composition is prepared by blending and deaerating the listed ingredients in standard fashion.

E. Chewing Gum

A chewing gum is prepared by replacing the sucrose normally added to chewing gum with the sweeteners of the present invention. A gum base is prepared from:

| Ingredients | Weight in Grams |
|---|---|
| 60% latex | 18 |
| Hydrogenated rosin esters | 44 |
| Paracumarine resin | 7.5 |
| Candellila wax | 6 |
| Glyceryl tristerate | 2.5 |
| Ethyl cellulose | 2 |
| Calcium carbonate | 20 |

The gum base is used with the sweeteners of the present invention to prepare a chewing gum having a greatly reduced sugar content.

| Ingredients | Percent by Weight |
| --- | --- |
| Gum base | 68 |
| Sweetener* | 0.6 |
| Corn syrup | 16 |
| Flavor | 1 |

*Example 3

Chewing gum can also be prepared using other sweeteners of the present invention.

F. Powdered Sweetener Concentrate

Sweetener of Example 3, Hydrochloride Salt: 6.4 mg.
Dextrose: 840 mg.

One packet containing the foregoing ingredients will be the approximate equivalent of two teaspoons of sugar.

H. Liquid Sweetener Concentrate

|  | Gm. % |
| --- | --- |
| Example 3, Hydrochloride salt | 0.12 |
| Benzoic acid | 0.1 |
| Methyl paraben | 0.05 |
| Water | Balance |

Ten drops provides the approximate sweetening power of one teaspoon of sugar.

What is claimed is:
1. endo-2-Amino-1,3,3-trimethyl-7-oxabicyclo[2.2.1]-heptane.
2. exo-2-Amino-1,3,3-trimethyl-7-oxabicyclo[2.2.1]-heptane.

* * * * *